(12) United States Patent
Wang et al.

(10) Patent No.: US 11,311,255 B2
(45) Date of Patent: Apr. 26, 2022

(54) MEDICAL DETECTORS AND MEDICAL IMAGING DEVICES

(71) Applicant: Shanghai Neusoft Medical Technology Co., Ltd., Shanghai (CN)

(72) Inventors: Xi Wang, Shanghai (CN); Xinying Li, Shanghai (CN); Jian Zhao, Shanghai (CN); Baowei Xu, Shanghai (CN); Guodong Liang, Shanghai (CN)

(73) Assignee: Shanghai Neusoft Medical Technology Co., Ltd., Shanghai (CN)

( * ) Notice: Subject to any disclaimer, the term of this patent is extended or adjusted under 35 U.S.C. 154(b) by 0 days.

(21) Appl. No.: 16/931,874

(22) Filed: Jul. 17, 2020

(65) Prior Publication Data

US 2021/0015436 A1 Jan. 21, 2021

(30) Foreign Application Priority Data

Jul. 19, 2019 (CN) .......................... 201910655205.6

(51) Int. Cl.
*A61B 6/00* (2006.01)
*G01T 1/20* (2006.01)
(Continued)

(52) U.S. Cl.
CPC ............ *A61B 6/4233* (2013.01); *A61B 6/037* (2013.01); *A61B 6/0407* (2013.01); *A61B 6/461* (2013.01);
(Continued)

(58) Field of Classification Search
CPC ..... A61B 6/4233; A61B 6/037; A61B 6/0407; A61B 6/461; G01T 1/20185; G01T 1/2002; G01T 1/202; G01T 1/2985
See application file for complete search history.

(56) References Cited

U.S. PATENT DOCUMENTS 4,831,263 A 5/1989 Yamashita
7,956,331 B2 6/2011 Lewellen et al.
(Continued)

FOREIGN PATENT DOCUMENTS

CN 102227649 A 10/2011
CN 104024887 A 9/2014
(Continued)

OTHER PUBLICATIONS

State Intellectual Property Office of the People's Republic of China, Office Action and Search Report Issued in Application No. 2019106552056, dated Jun. 28, 2020, 19 pages, (Submitted with Machine Translation).
(Continued)

*Primary Examiner* — Blake C Riddick
(74) *Attorney, Agent, or Firm* — Fish & Richardson P.C.

(57) ABSTRACT

Medical detectors and medical imaging devices are provided. In one aspect, a medical detector includes: a photoelectric conversion device, a first crystal array layer disposed over the photoelectric conversion device, and a second crystal array layer disposed over the first crystal layer. The first crystal array layer includes a plurality of first scintillation crystals arranged in a first crystal array, and a first coupling medium being filled between every adjacent two of the first scintillation crystals. The second crystal array layer includes a plurality of second scintillation crystals arranged in a second crystal array, and a second coupling medium being filled between every adjacent two of the second scintillation crystals. A light transmittance of the second coupling medium is different from a light transmittance of the first coupling medium.

16 Claims, 6 Drawing Sheets

(51) Int. Cl.
*A61B 6/03* (2006.01)
*A61B 6/04* (2006.01)
*G01T 1/202* (2006.01)
*G01T 1/29* (2006.01)

(52) U.S. Cl.
CPC ............ *G01T 1/2002* (2013.01); *G01T 1/202* (2013.01); *G01T 1/20185* (2020.05); *G01T 1/2985* (2013.01)

(56) References Cited

U.S. PATENT DOCUMENTS

| | | | | |
|---|---|---|---|---|
| 9,864,073 | B1* | 1/2018 | Kim | G01T 1/202 |
| 2002/0195565 | A1* | 12/2002 | Lecoq | G01T 1/202 |
| | | | | 250/363.03 |
| 2004/0129886 | A1* | 7/2004 | Lecoq | G01T 1/2985 |
| | | | | 250/363.03 |
| 2004/0227091 | A1* | 11/2004 | LeBlanc | G01T 1/1642 |
| | | | | 250/366 |
| 2008/0210877 | A1* | 9/2008 | Altman | A61B 6/032 |
| | | | | 250/366 |
| 2009/0261262 | A1* | 10/2009 | Hunt | G01T 1/2002 |
| | | | | 250/370.11 |
| 2010/0135463 | A1* | 6/2010 | Kang | G01T 1/2018 |
| | | | | 378/98.9 |
| 2010/0148074 | A1* | 6/2010 | Menge | G01T 1/1644 |
| | | | | 250/362 |
| 2010/0155610 | A1* | 6/2010 | Menge | G01T 1/2002 |
| | | | | 250/368 |
| 2010/0220833 | A1* | 9/2010 | Levene | G01T 1/2018 |
| | | | | 378/19 |
| 2010/0270463 | A1 | 10/2010 | Lee et al. | |
| 2011/0263965 | A1* | 10/2011 | Kang | G01T 1/2985 |
| | | | | 600/411 |
| 2011/0297834 | A1* | 12/2011 | Komori | A61B 6/4417 |
| | | | | 250/363.03 |
| 2012/0001075 | A1* | 1/2012 | Frach | G01T 1/2002 |
| | | | | 250/362 |
| 2012/0061576 | A1* | 3/2012 | Degenhardt | G01T 1/2018 |
| | | | | 250/362 |
| 2012/0061577 | A1* | 3/2012 | Oleinik | G01T 1/2018 |
| | | | | 250/366 |
| 2013/0092840 | A1* | 4/2013 | Ohta | G03B 42/025 |
| | | | | 250/361 R |
| 2013/0299707 | A1* | 11/2013 | Levin | G01T 1/1642 |
| | | | | 250/363.03 |
| 2014/0158891 | A1* | 6/2014 | Perna | G01T 1/20 |
| | | | | 250/366 |
| 2015/0028218 | A1* | 1/2015 | Kataoka | G01T 1/1642 |
| | | | | 250/367 |
| 2015/0331117 | A1* | 11/2015 | Ho | G01T 1/2008 |
| | | | | 250/367 |
| 2016/0109586 | A1* | 4/2016 | Eguchi | G01T 1/2006 |
| | | | | 250/361 R |
| 2016/0109587 | A1* | 4/2016 | Wieczorek | G01T 1/2018 |
| | | | | 250/362 |
| 2016/0223687 | A1* | 8/2016 | Yamashita | G01T 1/20 |
| 2017/0164915 | A1* | 6/2017 | Li | A61B 6/0435 |
| 2017/0192107 | A1* | 7/2017 | Li | A61B 6/032 |
| 2018/0100101 | A1* | 4/2018 | Kurosawa | H01L 31/0232 |
| 2018/0196146 | A1* | 7/2018 | Fukuta | C09K 11/7774 |
| 2018/0242927 | A1* | 8/2018 | Nakai | A61B 6/4208 |
| 2018/0292548 | A1* | 10/2018 | Zhang | A61B 6/037 |
| 2019/0120976 | A1* | 4/2019 | Wu | G01T 1/202 |

FOREIGN PATENT DOCUMENTS

| | | |
|---|---|---|
| CN | 107121692 A | 9/2017 |
| CN | 107735694 A | 2/2018 |
| CN | 109782326 A | 5/2019 |

OTHER PUBLICATIONS

Huang et al., "Nuclear Medicine and Molecular Imaging," Shanghai Jiao Tong University Press, Feb. 29, 2006, p. 57, 3 pages total (with English Translation).

Liu et al., "Development of PET scanner for small animals," Chinese Medical Equipment Journal, Dec. 31, 2007, 28(6), 4 pages (with English Abstract).

Office Action in Chinese Appln. No. 201910655205.6, dated Aug. 16, 2021, 17 pages (with Machine Translation).

* cited by examiner

MEDICAL DETECTORS AND MEDICAL IMAGING DEVICES

CROSS REFERENCE TO RELATED APPLICATIONS

This application claims priority to Chinese Patent Application No. 201910655205.6 entitled "MEDICAL DETECTOR AND MEDICAL IMAGING DEVICE" filed on Jul. 19, 2019, the entire content of which is incorporated herein by reference.

TECHNICAL FIELD

The present disclosure relates to the field of medical equipment technology, particularly to medical detectors and medical imaging devices.

BACKGROUND

PET (Positron Emission Tomography) is one of the most advanced medical diagnostic equipment at present. It utilizes the principle that by injecting compounds (imaging agents) having labeled isotopes by positron emission into a human body, such as one or two isotopes of carbon, oxygen, nitrogen and nitrogen, and when participating in physiological metabolism of the human body, these labeled compounds will have an annihilation effect which generates two γ rays emitted back-to-back with an energy of 511 keV.

Depending on the ability of different parts of the human body to absorb the labeled compound, the concentration of isotopes in different parts of the human body is different, and the intensity of photons produced by the annihilation reaction is also different. With a γ particle detector surrounding the human body, the time, position, number and direction of photons released by the energy conversion of γ particles can be detected. The optical signal is converted into a current or voltage pulse signal by a photoelectric conversion device, and the signals are collected, digital/analog converted, stored, calculated, and image reconstructed by an electronic collecting system and a computer system so as to obtain a cross-sectional image of the human organs, a coronal cross-sectional image or a sagittal cross-sectional image. Tissues or lesions with high metabolic rate can display bright signals of high metabolic on PET, while tissues or lesions with low metabolic rate can display dark signals of low metabolic on PET.

SUMMARY

The present disclosure provides medical detectors and medical imaging devices, which can ensure the accuracy of the depth of interaction (DOI) of the energy conversion of the γ particles in the crystal.

According to a first aspect of the embodiments of the present disclosure, a medical detector is provided, including: a photoelectric conversion device; a first crystal array layer disposed over the photoelectric conversion device, the first crystal array layer comprising a plurality of first scintillation crystals arranged in a first crystal array, a first coupling medium being filled between every adjacent two of the first scintillation crystals; and a second crystal array layer disposed over the first crystal array layer, the second crystal array layer comprising a plurality of second scintillation crystals arranged in a second crystal array, a second coupling medium being filled between every adjacent two of the second scintillation crystals, wherein a first light transmittance of the first coupling medium is different from a second light transmittance of the second coupling medium.

In an example, a higher one of the first and second light transmittances is no lower than 70%, and a lower one of the first and second light transmittances is no higher than 10%.

In an example, a crystal material of the first scintillation crystal is the same as a crystal material of the second scintillation crystal.

In an example, a crystal material of the first scintillation crystal is different from a crystal material of the second scintillation crystal.

In an example, the medical detector further includes adhesive material disposed between the plurality of first scintillation crystals of the first crystal array layer and the plurality of second scintillation crystals of the second crystal array layer.

In an example, the medical detector further includes adhesive material disposed between the plurality of first scintillation crystals of the first crystal array layer and the photoelectric conversion device.

In an example, the medical detector further includes a light guide adhesively arranged between the first crystal array layer and the photoelectric conversion device.

In an example, the first crystal array layer includes a bottom surface bonded to the photoelectric conversion device, a top surface bonded to a bottom surface of the second crystal array layer, and side surfaces, together with side surfaces of the second crystal array and a top surface of the second crystal array layer, covered with a reflective layer.

In an example, a light transmittance of the reflective layer is no greater than 10%.

In an example, each of the first scintillation crystals includes a crystal selected from a group including: a lutetium silicate crystal, an yttrium lutetium silicate crystal, a lutetium fine silicate crystal, a gadolinium silicate crystal, a lanthanum bromide crystal, a gadolinium aluminum gallium garnet crystal, and a cerium-doped yttrium aluminate crystal. Each of the first scintillation crystals can have a same crystal specification. Each of the second scintillation crystals includes a crystal selected from a group including: a lutetium silicate crystal, an yttrium lutetium silicate crystal, a lutetium fine silicate crystal, a gadolinium silicate crystal, a lanthanum bromide crystal, a gadolinium aluminum gallium garnet crystal, and a cerium-doped yttrium aluminate crystal. Each of the second scintillation crystals can have a same crystal specification. In some cases, each of the first scintillation crystals and each of the second scintillation crystals can be made of a same crystal material.

In an example, an array arrangement of the second crystal array is same as that of the first crystal array, and a center distance of adjacent two of the second scintillation crystals is same as that of adjacent two of the first scintillation crystals.

According to a second aspect of the embodiments of the present disclosure, a medical imaging device is provided, including a detection ring assembled by assembling a plurality of medical detectors, a centralized data managing board, a reconstruction processor, a display, and a scanning bed. Each of the plurality of medical detectors can be the medical detector as described in any one of the first aspect of the embodiments.

According to a third aspect of the embodiments of the present disclosure, a medical detector is provided, including: a photoelectric conversion device; and a crystal array disposed over a photoelectric conversion device, the crystal array comprising a plurality of scintillation crystals arranged in an array, the crystal array being divided into a first crystal region and a second crystal region along a length direction of the scintillation crystals, the first crystal region comprising first parts of the scintillation crystals and the second crystal region comprising second parts of the scintillation crystals; a first coupling medium being filled between the first parts of every adjacent two of the scintillation crystals in the first crystal region, and a second coupling medium being filled between the second parts of every adjacent two of the scintillation crystals in the second crystal region, and wherein a first light transmittance of the second coupling medium is different from that of the first coupling medium.

In an example, a higher one of the first and second light transmittances is no lower than 70%, and a lower one of the first and second light transmittances is no higher than 10%.

In an example, a bottom surface of the crystal array is bonded to the photoelectric conversion device, and wherein side surfaces of the crystal array and a top surface of the crystal array are all covered with a reflective layer.

In an example, the medical detector further includes adhesive material disposed between the plurality of scintillation crystals of the crystal array and the photoelectric conversion device.

In an example, the medical detector further includes a light guide adhesively arranged between the crystal array and the photoelectric conversion device.

In an example, each of the plurality of scintillation crystals is selected from a group comprising: a lutetium silicate crystal, an yttrium lutetium silicate crystal, a lutetium fine silicate crystal, a gadolinium silicate crystal, a lanthanum bromide crystal, a gadolinium aluminum gallium garnet crystal, and a cerium-doped yttrium aluminate crystal.

According to a fourth aspect of the embodiments of the present disclosure, a medical imaging device is provided, including a detection ring assembled by assembling a plurality of medical detectors, a centralized data managing board, a reconstruction processor, a display, and a scanning bed. Each of the plurality of medical detectors can be the medical detector as described in any of the third aspect of the embodiments.

It can be seen from the above technical solutions that, in the medical detector of the present disclosure, by using coupling materials with different light transmittances between the first scintillation crystals of the first crystal array layer and between the second scintillation crystals of the second crystal array layer, the diffusion degree of the γ particles in the first scintillation crystals and the second scintillation crystals is different, therefore the waveforms of the optical signals generated by the energy conversion of the γ particles in the first scintillation crystals and the second scintillation crystals are different, thereby displaying different waveform characteristics on the photoelectric conversion device, so that in which layer of crystals in the detector the γ particles are obtained can be accurately determined, and the accuracy of the DOI of the γ particles when converting energy in the crystals can be ensured.

The details of one or more examples of the subject matter described in the present disclosure are set forth in the accompanying drawings and description below. Other features, aspects, and advantages of the subject matter will become apparent from the description, the drawings, and the claims. Features of the present disclosure are illustrated by way of example and not limited in the following figures, in which like numerals indicate like elements.

DETAILED DESCRIPTION

A critical step in PET imaging is the collection of γ signals. How to accurately obtain the position information of the captured γ particles is one of the critical factors that determine the quality of PET imaging. During the collecting process of PET data, two γ signals with an energy of 511 keV captured in a same time window are identified as two γ particles generated by a same isotope annihilation event, and a line connecting the positions of the two captured γ particles is referred to as a line of response (LOR). It is considered that this isotope annihilation event occurred on this response line.

Due to the high energy and strong penetration ability of γ particles, to improve the detection efficiency, PET equipment has to use scintillation crystals with a certain thickness. For example, the thickness of the commonly used scintillation crystal is 15 mm-30 mm. The thickness of the scintillation crystal may cause "parallax error" problem, that is, in the margin area of the field of view, there is an error between the response line and the trajectory of the γ particle flying line, which causes the resolution of the PET image to significantly decrease in the margin area of the image.

In the process of capturing γ particles, the depth information (depth of interaction, DOI) of γ particles when converting energy in scintillation crystals is obtained at the same time, which can be used to effectively reduce parallax errors and improve the resolution of the margin area of the PET image, thereby improving the image quality. However, the accuracy of the DOI of the γ particles obtained by current PET cannot be easily ensured.

Implementations of the present disclosure provide medical detectors and medical imaging devices that can ensure accuracy of depth of interaction (DOI) of the energy conversion of γ particles in crystals, thereby ensuring the imaging quality. The medical detectors and medical imaging devices will be described in detail below with reference to the drawings. In the case of no conflict, the features in the following embodiments and implementations can be in any suitable combination thereof.

Figure 1:
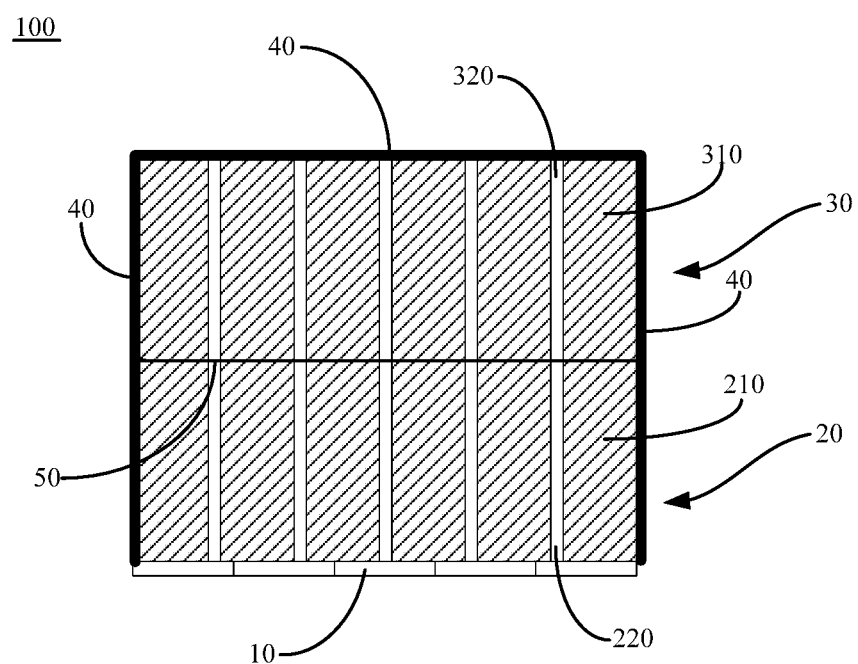
FIG. 1 illustrates a schematic structural diagram of a medical detector of an embodiment of the present disclosure.

FIG. 1 shows a medical detector 100 that can be used as a DOI detector in a PET device. The medical detector 100 may include: a photoelectric conversion device 10, a first crystal array layer 20, and a second crystal array layer 30.

The first crystal array layer 20 is disposed over (above or on top of) the photoelectric conversion device 10. The first crystal array layer 20 includes a plurality of first scintillation crystals 210 which are arranged in an array, and a first coupling medium 220 is filled between every adjacent two of the first scintillation crystals 210.

The second crystal array layer 30 is disposed over the first crystal array layer 20. The second crystal array layer 30 includes a plurality of second scintillation crystals 310 which are arranged in an array. A second coupling medium 320 is filled between every adjacent two of the second scintillation crystals 310. A light transmittance of the second coupling medium 320 can be different from that of the first coupling medium 220.

It should be noted that the crystal material of the first scintillation crystal 210 and the second scintillation crystal 310 may be a same crystal material or different crystal materials. Adhesive material can be provided between the photoelectric conversion device 10, the first crystal array layer 20, and the second crystal array layer 30 as described in detail below.

By using coupling materials with different light transmittances between the scintillation crystals of the first crystal array layer 20 and between the scintillation crystals of the second crystal array layer 30, respectively, the diffusion degrees of the γ particles in the first scintillation crystals 210 and the second scintillation crystals 310 can be different. Accordingly, the waveforms of the optical signals generated by the energy conversion of the γ particles in the first scintillation crystals 210 and the second scintillation crystal 310 can be different, thereby displaying different waveform characteristics on the photoelectric conversion device 10. In such a way, a layer of crystals in the detector in which they particles are obtained can be accurately determined, and thus the accuracy of the depth of interaction (DOI) information when the γ particles convert energy in the crystals can be ensured, thereby ensuring imaging quality.

In an optional example, the photoelectric conversion device 10 may be a SiPM (Silicon Photomultipliers) device which has a compact structure and high signal-to-noise ratio that greatly improve the spatial resolution of the PET device. Its fast time response characteristic can meet the technical requirements of TOF-PET (time of flight-TOF) and improve the detection efficiency of the detector. The photoelectric conversion device 10 may adopt an array arrangement of K×L, where K and L are both positive integers greater than 1. A signal of the photoelectric conversion device 10 can be read after being converted into four "centroid signals" through a resistance/capacitance network circuit (Discretized Positioning Circuit, DPC), or it can be read separately at a ratio of 1:1.

Correspondingly, each of the first scintillation crystals 210 may include a crystal selected from a group including: a LSO crystal (lutetium silicate crystal), a LYSO crystal (yttrium lutetium silicate crystal), a LFS crystal (lutetium fine silicate crystal), a LaBr3 crystal (bromine Lanthanum crystal), a GSO crystal (gadolinium silicate crystal), a GAGG crystal (gadolinium aluminum gallium garnet crystal), a Ce:YAP crystal (cerium-doped yttrium aluminate crystal) and other crystal materials. Each of the second scintillation crystals 310 may also include a crystal selected from the above group. Such crystal materials in the group are all fast crystals that are commonly used to meet the technical requirements of TOF.

When both the first scintillation crystal 210 and the second scintillation crystal 310 are fast crystals, for example, the first scintillation crystal 210 is an LSO crystal with a decay time constant of 40 ns (typical value), and the second scintillation crystal 310 is an LYSO crystal with a decay time constant of 42 ns (typical value), the optical signals generated by the energy conversion of the γ particles in different scintillation crystals can have different characteristics, for example, the decay times for the optical signals can be different. By determining corresponding characteristics of the optical signal, the DOI of the γ particles when converting energy in the crystals can be obtained.

In some cases, the first coupling medium 220 and the second coupling medium 320 are coupling materials with a same light transmittance. Since the difference between the decay times of light signals of the first scintillation crystal 210 and the second scintillation crystal 310 is too small, the waveform characteristics of their light output are very similar, which is difficult to be distinguished accurately, so that the accuracy of the DOI of the γ particles when converting energy in the crystals cannot be easily ensured.

To ensure the accuracy of the DOI of the γ particles when converting energy in the crystals, in some cases, one of the first scintillation crystal 210 and the second scintillation crystal 310 is replaced with slow crystal, such as BGO (bismuth germanate crystals) with a decay time constant of 300 ns, so that its light output waveform can be significantly different from a fast crystal, e.g., an LSO crystal or an LYSO crystal. However, when ½ of the crystals in the detector are such slow crystals, the time system may be seriously deteriorated, and it is difficult to realize the TOF function.

In some cases, in the medical detector 100, the first coupling medium 220 and the second coupling medium 320 can be coupling materials with different light transmittances, and the diffusion degree of the γ particles in the first scintillation crystals 210 310 can be different from that in the second scintillation crystals. That is, the signal waveforms of the optical signals generated by the energy conversion of the γ particles in the first scintillation crystals 210 and the second scintillation crystals 310 can be different. Accordingly, different waveform characteristics can be displayed on the photoelectric conversion device 10, and a layer of crystals in the detector in which the γ particles are obtained can be accurately determined, and the accuracy of the DOI of the γ particles when converting energy in the crystals can be efficiently ensured, thereby ensuring the imaging quality. Therefore, in some cases, on the premise of ensuring that the TOF function can be realized, the crystal materials of the first scintillation crystal 210 and the second scintillation crystal 310 can be different crystal materials, for example, two fast crystals of LSO crystal and LYSO crystal which do not affect the accuracy of the DOI of the γ particles when converting energy in the crystals. In some other cases, the crystal materials of first scintillation crystal 210 and the second scintillation crystal 310 in the present disclosure can be a same crystal material, and the accuracy of the DOI of the γ particles when converting energy in the crystals may not be affected either, which can also facilitate the production, procurement and assembly of a same batch.

In a first implementation, the light transmittance of the first coupling medium 220 may be higher than the light transmittance of the second coupling medium 320. In a second implementation, the light transmittance of the first coupling medium 220 may be lower than the light transmittance of the second coupling medium 320. A relative higher one among respective light transmittances of the first coupling medium 220 and the second coupling medium 320 is no lower than 70%, and a relative lower one among respective light transmittances of the first coupling medium 220 and the second coupling medium 320 is no higher than 10%. These two implementations or configurations can have a same effect on the accuracy of the DOI of the γ particles when converting energy in the crystals. Optionally, the coupling materials having a higher light transmittance may include air, optical glue, OCA (Optically Clear Adhesive)

glue, etc. The coupling materials having a lower light transmittance may include $BaSO_4$, ESR film, $TiO_2$, etc.

In an optional implementation, the array arrangement of the second crystal array layer 30 is the same as that of the first crystal array layer 20. For example, a center distance of adjacent two of the second scintillation crystals 310 (may also be understood as a distance of the center points of two adjacent crystals) can be the same as that of adjacent two of the first scintillation crystals 210, so that the positions of a plurality of second scintillation crystals 310 correspond to the positions of a plurality of first scintillation crystals 210 one by one. In some cases, when the coupling medium is, for example, $BaSO_4$ or ESR film, since the $BaSO_4$ or ESR film itself has a thickness, the crystal size of the crystal layer coupled with $BaSO_4$ or ESR film may be slightly smaller than the crystal size of the crystal layer coupled with air, to reserve space for disposing $BaSO_4$ or ESR film.

In an optional implementation, both the first crystal array layer 20 and the second crystal array layer 30 may be matrix arrays. The array arrangement of the second crystal array layer 30 can be the same as that of the first crystal array layer 20. For example, the first crystal array layer 20 can be an N×M array, and the second crystal array layer 30 can be also an N×M array, where the arrangement directions of N columns and M columns are consistent, and N and M are positive integers greater than 1. The crystal specification of the plurality of second scintillation crystals 310 may be the same, and the crystal specification of the plurality of first scintillation crystals 210 may also be the same, so that the crystals can be produced in batches of the same specification, which can be convenient for the production, processing and assembly and easy to be manufactured. In this way, it can be better ensured that the positions of the plurality of second scintillation crystals 310 of the second crystal array layer 30 one by one correspond to that of the plurality of first scintillation crystals 210 of the first crystal array layer 20, which can thereby ensure that the external appearance of the detector is smooth and aesthetic.

In some cases, a PET detector can be produced with two crystal array layers, but in general, the two crystal array layers can include scintillation crystals of a same crystal material. The upper and lower crystal array layers can have different array arrangements. For example, the lower crystal array layer can have an array arrangement of N×M, and the upper crystal array layer can have an array arrangement of (N−1)×(M−1). The scintillation crystals of the upper and lower layer are staggered by half of a crystal size. In this way, the upper and lower crystal array layers may display different position points on the detector's position spectrum. By checking the position spectrum, the system can determine whether the γ particles are captured by the scintillation crystals of the upper crystal array layer or by the scintillation crystals of the lower crystal array layer. However, when a plurality of PET detectors are assembled into a PET detection ring, due to its irregular shape, large gaps are inevitably generated in both a ring direction and an axial direction. These gaps may significantly reduce the efficiency of the detector of PET system and lower the sensitivity of the system.

In some cases, in the medical detector 100 according to one or more implementations of the present disclosure, the array arrangement of the second crystal array layer 30 is the same as that of the first crystal array layer 20, and a center distance of adjacent two of the second scintillation crystals 310 is the same as that of adjacent two of the first scintillation crystals 210, so that positions of the plurality of second scintillation crystals 310 correspond to that of the plurality of first scintillation crystals 210 one by one, which not only ensure that the external appearance of the detector is smooth and aesthetic, but also ensure that there is no gap in either the ring direction or the axial direction when a plurality of medical detectors 100 are assembled into a detection ring, so that the detection efficiency of the detector and the sensitivity of the system can be efficiently improved.

In an optional implementation, a bottom surface of the first crystal array layer 20 is bonded to the photoelectric conversion device 10, and a top surface of the first crystal array layer 20 is bonded to a bottom surface of the second crystal array layer 30. The side surfaces of the first crystal array layer 20, the side surfaces of the second crystal array layer 30, and the top surface of the second crystal array layer 30 are all covered with a reflective layer 40. The reflective layer 40 can completely cover the first crystal array layer 20 and the second crystal array layer 30, so as to effectively prevent the external light from entering the detector and affecting the luminous effect of the γ particles in the crystals, and to improve the light collecting efficiency of the detector to ensure the accuracy of the detector. In this embodiment, the reflective layer 40 may include a reflective material with smaller light transmittance, such as barium sulfate ($BaSO_4$), ESR film (3M™ Enhanced Specular Reflector), titanium dioxide ($TiO_2$), Teflon (Teflon), etc. In some examples, the light transmittances of these materials are not higher than 10%, which can almost achieve an effect of opacity.

It should be noted that the bottom surface of the first crystal array layer 20 can be understood as being formed by all the bottom surfaces of the first scintillation crystals 210. The top surface of the first crystal array layer 20 can be understood as being formed by all the top surfaces of the first scintillation crystals 210. The side surfaces of the first crystal array layer 20 can be understood as being formed by the outer side surfaces of the first scintillation crystals 210 located at the outermost side of the first crystal array layer 20. The bottom surface of the second crystal array layer 30 can be understood as being formed by all the bottom surfaces of the second scintillation crystals 310, and the top surface of the second crystal array layer 30 can be understood as being formed by all the top surfaces of the second scintillation crystals 310, the side surfaces of the second crystal array layer 30 can be understood as being formed by the outer side surfaces of the second scintillation crystal 310 located at the outermost side of the second crystal array layer 30.

Taking an example that both the first crystal array layer 20 and the second crystal array layer 30 are arranged as a cube array, four outer side surfaces of the first crystal array layer 20, four outer side surfaces of the second crystal array layer 30 and the top surface of the second crystal array layer 30 are all covered with a reflective layer 40. The reflective layer 40 of the four outer side surfaces of the first crystal array layer 20 and the four outer side surfaces of the second crystal array layer 30 may be integrally formed for the convenience of operations.

In an optional implementation, adhesive material can be provided between the plurality of first scintillation crystals 210 of the first crystal array layer 20 and the plurality of second scintillation crystals 310 of the second crystal array layer 30, that is, an adhesive layer 50 can be formed between the first crystal array layer 20 and the second crystal array layer 30. Optionally, the adhesive material may be an adhesive material with a low refractive index (for example, ≤1.8) and a high light transmittance (for example, ≥70%), such as glue liquid, glue film or air. The adhesive layer 50 can further generate refraction, so that the DOI of γ particles when converting energy in the second scintillation crystals 310 can be better distinguished from the DOI when converting energy in the first scintillation crystals 210.

In addition, adhesive material can be provided between the plurality of first scintillation crystals 210 of the first crystal array layer 20 and the photoelectric conversion device 10. Optionally, the adhesive material may be an adhesive material with a low refractive index (for example, ≤1.8) and a high light transmittance (for example, ≥70%), such as glue liquid, glue film or air. Using such adhesive material may not affect the projection shape formed on the photoelectric conversion device 10 by the DOI of the γ particles when converting energy in the crystals.

In an optional implementation, the medical detector 100 may further include a light guide component (or a light guide), e.g., an optical waveguide. The light guide component may be disposed between the first crystal array layer 20 and the photoelectric conversion device 10 by using the adhesive material, that is, the plurality of first scintillation crystals 210 of the first crystal array layer 20 and the photoelectric conversion device 10 can both be bonded to the light guide component by the adhesive material. The light guide component can improve the uniformity of crystal light emission. Optionally, the light guide component may be made of glass, and its thickness may be set according to actual needs.

Figure 2A:
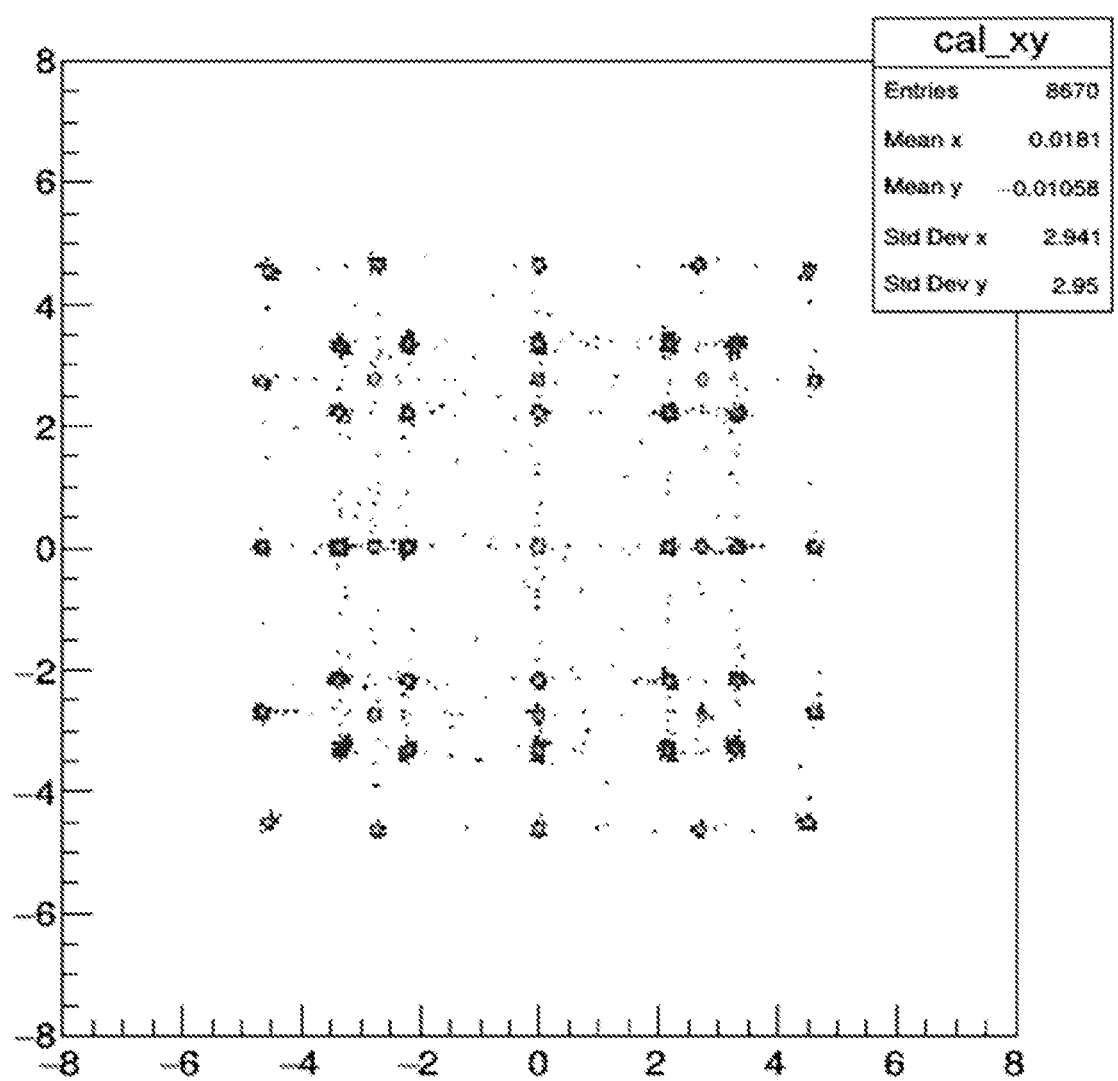
FIGS. 2A and 2B illustrate respectively a position spectrum of a medical detector of an embodiment of the present disclosure.

FIG. 2A illustrates an example position spectrum of the medical detector 10, in which both the first crystal array layer 20 and the second crystal array layer 30 have an array arrangement of 5×5. The size of the first scintillation crystal 210 and the second scintillation crystal 310 are both 3.2 mm×3.2 mm×9 mm. Coupling materials with lower light transmittance (for example, $BaSO_4$) are filled between the first scintillation crystals 210 of the first crystal array layer 20, and coupling materials with higher light transmittance (for example, air) are filled between the second scintillation crystals 310 of the second crystal array layer 30. The photoelectric conversion device 10 is a 4×4 array of SiPM.

Figure 2B:
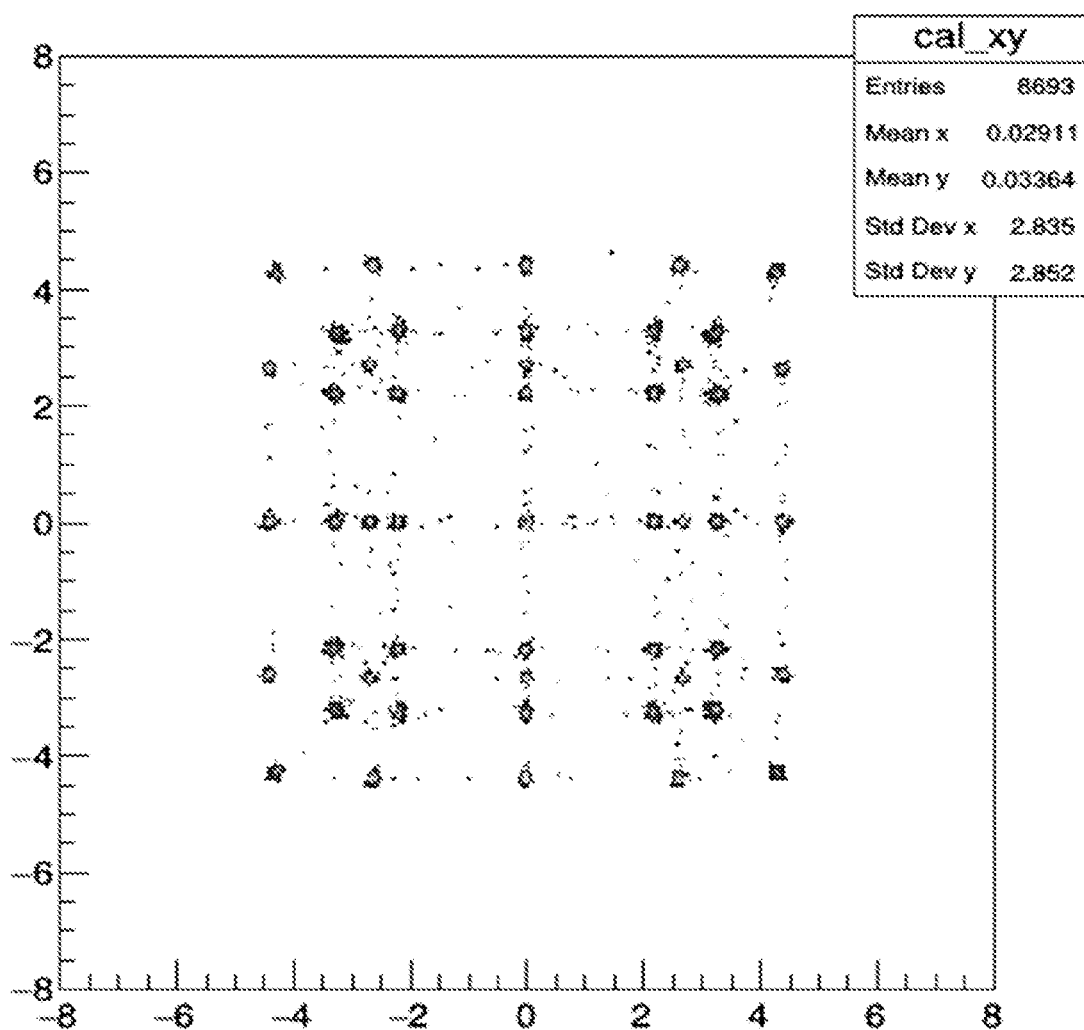

FIG. 2B illustrates another example position spectrum of the medical detector 10, in which both the first crystal array layer 20 and the second crystal array layer 30 have an array arrangement of 5×5. The size of the first scintillation crystal 210 and the second scintillation crystal 310 are both 3.2 mm×3.2 mm×9 mm, where the scintillation crystals are LYSO crystals. Coupling materials with higher light transmittance (for example, air) are filled between the first scintillation crystals 210 of the first crystal array layer 20, and coupling materials with lower light transmittance (for example, $BaSO_4$) are filled between the second scintillation crystals 310 of the second crystal array layer 30. The photoelectric conversion device 10 is a 4×4 array of SiPM.

It can be seen from FIGS. 2A and 2B that, under these two settings, the two crystal array layers both have an array arrangement of 5×5, so there are 50 position points in total, in which 49 position points can be clearly distinguished in the position spectrum diagram. Since the photoelectric conversion device 10 is a 4×4 array of SiPM, the central crystal is in a center symmetrical state, and the corresponding positions of the central crystals of the first crystal array layer 20 and the second crystal array layer 30 on the position spectrum are coincident.

No matter the light transmittance of the first coupling medium 220 is higher than that of the second coupling medium 320, or the light transmittance of the first coupling medium 220 is lower than that of the second coupling medium 320, that is, regardless of which of the transmittance of the coupling material filled between the first scintillation crystals 210 of the first crystal array layer 20 and the coupling material filled between the second scintillation crystals 310 of the second crystal array layer 30 is higher, the position spectrum of the projection of the DOI of the γ particles, when converting energy in the crystals on the photoelectric conversion device, can display both a larger 5×5 matrix and a smaller 5×5 matrix, which can distinguish the DOI of the γ particles when converting energy in the crystals well, so that the accuracy can be ensured.

Figure 3:
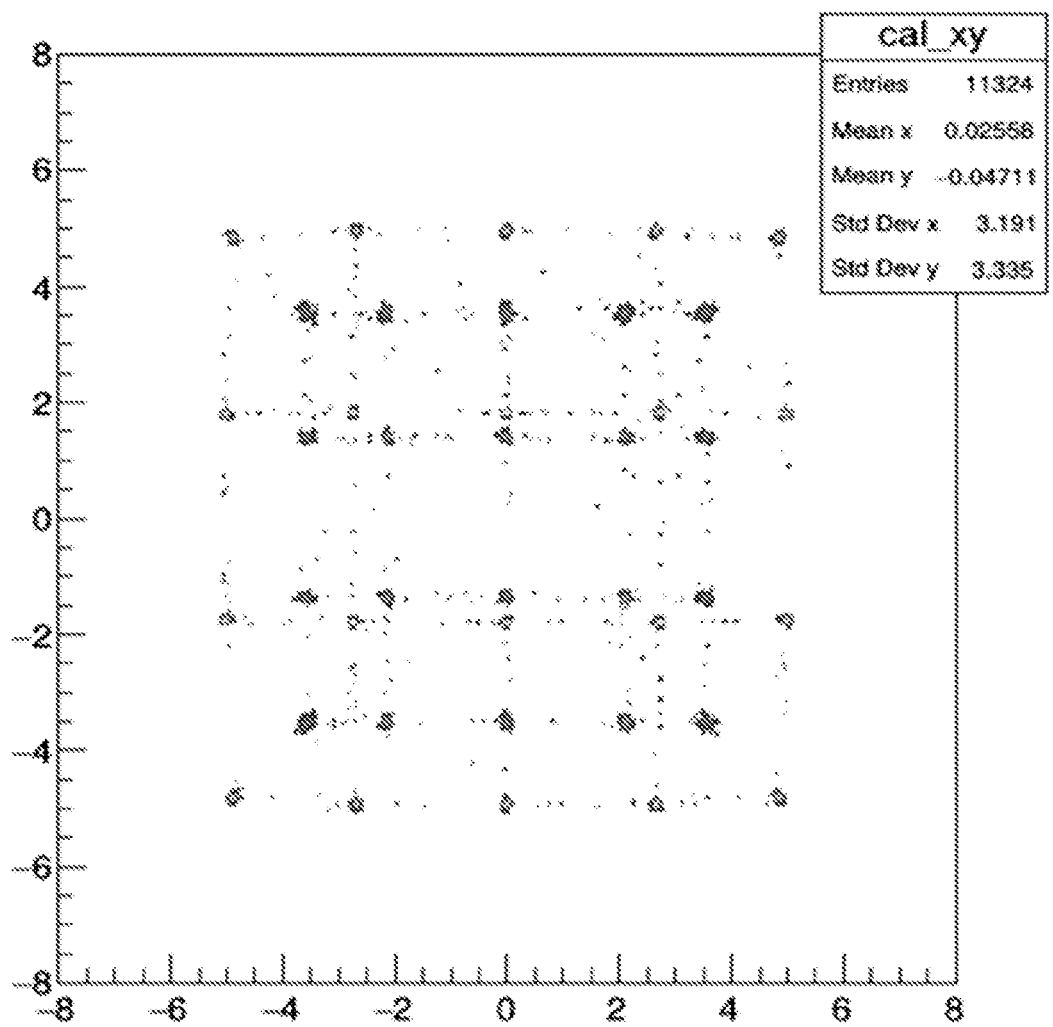
FIG. 3 illustrates a position spectrum of another medical detector of an embodiment of the present disclosure.

Referring to FIG. 3, each of the first crystal array layer 20 and the second crystal array layer 30 has an array arrangement of 4×5. The size of each of the first scintillation crystal 210 and the second scintillation crystal 310 is 4 mm×3.2 mm×9 mm, where the scintillation crystals are LYSO crystals. Coupling materials with lower light transmittance (for example, $BaSO_4$) are filled between the first scintillation crystals 210 of the first crystal array layer 20, and coupling materials with higher light transmittance (for example, air) are filled between the second scintillation crystals 310 of the second crystal array layer 30.

It can be seen from FIG. 3 that the crystals are arranged in a 4×5 array. The position spectrum of a projection of the DOI of the γ particles when converting energy in the crystals on the photoelectric conversion device can display both a larger 4×5 matrix and a smaller 4×5 matrix, so each array has 40 position points in total, in which the DOI of the γ particles when converting energy in the crystals can be distinguished well and the accuracy can be ensured.

In the medical detector 100 according to one or more embodiments of the present disclosure, coupling materials with different light transmittances are used between the first scintillation crystals of the first crystal array layer 20 and between the second scintillation crystals of the second crystal array layer 30, so that even the first scintillation crystal 210 and the second scintillation crystal 310 are same type of scintillation crystals, the acquisition for the DOI information of the γ particles can be realized, and the TOF function can be maintained at the same time. The array arrangement of the second crystal array layer 30 is the same as that of the first crystal array layer 20, and the center distance between adjacent two of the second scintillation crystals 310 is the same as that between adjacent two of the first scintillation crystals 210, so that the positions of the plurality of second scintillation crystals 310 correspond to the positions of the plurality of first scintillation crystals 210 one by one. In this way, when a plurality of medical detectors 100 are assembled into a detection ring of the PET system, there is no gap between two adjacent medical detectors 100 and the detection efficiency may not be reduced. No additional expansion or development is required for photoelectric conversion device, back-end processing circuits, computing processing ability, and electronics, and there is little impact on cost and engineering development.

Figure 4:
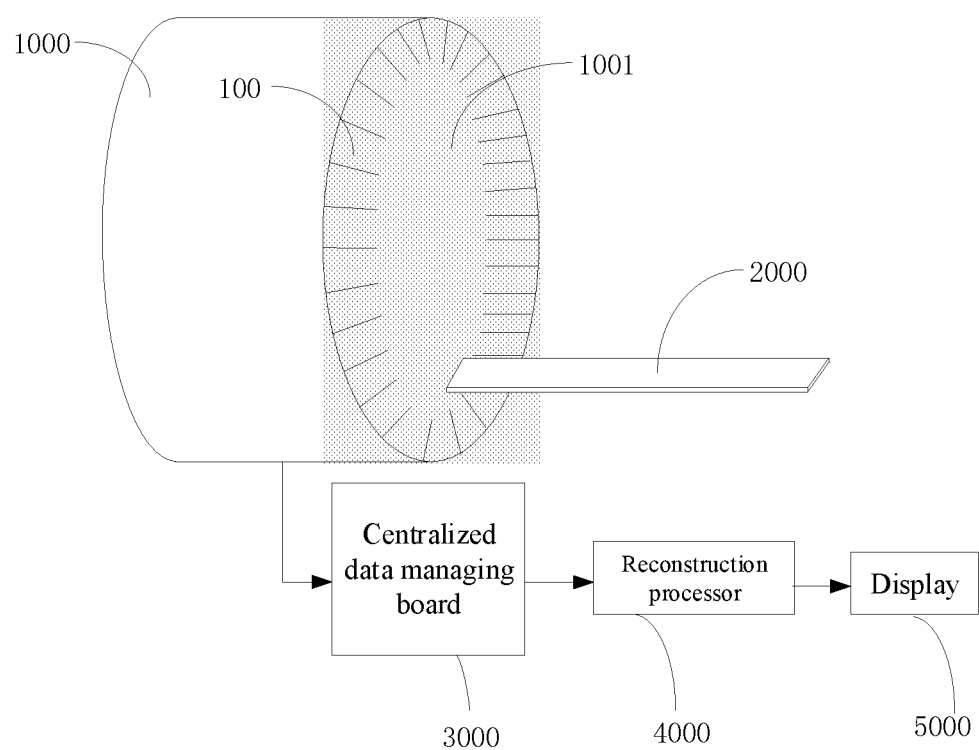
FIG. 4 illustrates a schematic structural diagram of a medical imaging device of an embodiment of the present disclosure.

Referring to FIG. 4, an embodiment of the present disclosure also provides a medical imaging device, including a detection ring 1000 assembled by assembling a plurality of medical detectors 100, a scanning bed 2000, a centralized data managing board 3000, a reconstruction processor 4000 and a display 5000. A detection area 1001 is formed inside the detection ring 1000. The scanning bed 2000 can slide relative to the detection area 1001. The driving structure of the scanning bed 2000 is not shown. The centralized data managing board 3000 is connected to the detectors 100 and the reconstruction processor 4000 respectively. Electrical signals formed from the γ particles in the detectors 100 are processed by the centralized data managing board 3000 and, for example, if a coincidence event is determined, the processed data may be transmitted to the reconstruction processor 4000. The reconstruction processor 4000 performs image reconstruction and displays the reconstructed image through the display 5000. It should be noted that the description of the medical detector 100 in the above-mentioned embodiments and examples is also applicable to the medical imaging device in FIG. 4.

Figure 5:
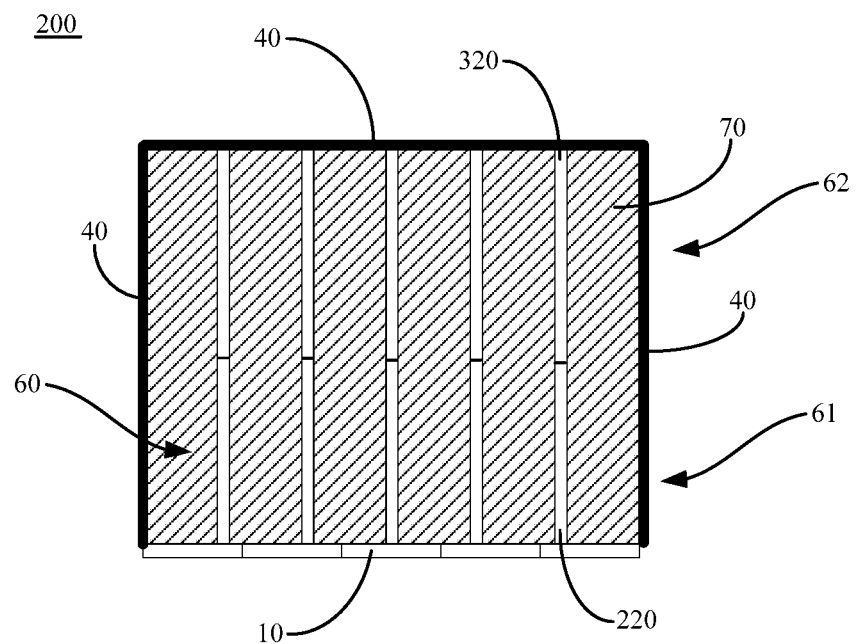
FIG. 5 illustrates a schematic structural diagram of another medical detector of an embodiment of the present disclosure.

FIG. 5 shows another example medical detector 200 according to one or more implementations of the present disclosure. The medical detector 200 can be used as a DOI detector in a PET device. The medical detector 200 may include: a photoelectric conversion device 10 and a crystal array 60.

The crystal array 60 is disposed over the photoelectric conversion device 10. The crystal array 60 includes a plurality of scintillation crystals 70 which are arranged in an array. The crystal array 60 is divided into a first crystal region 61 and a second crystal region 62 along the length direction of the scintillation crystals 70. A first coupling medium 220 is filled between parts of every adjacent two of the scintillation crystals 70 in the first crystal region 61, and a second coupling medium 320 is filled between parts of every adjacent two of the scintillation crystals 70 in the second crystal region 62. A light transmittance of the second coupling medium 220 is different from that of the first coupling medium 320. It should be noted that adhesive material can be provided between the photoelectric conversion device 10 and the crystal array 60 as described in detail below. In this embodiment, the first crystal region 61 is arranged to be close to the photoelectric conversion device 10.

By using coupling materials with different light transmittances between the scintillation crystals 70 in the first crystal region 61 and between the scintillation crystals 70 in the second crystal region 62 of the crystal array 60, respectively, the signal waveform of the optical signal generated by the energy conversion of the γ particles in the scintillation crystals 70 of the first crystal region 61 and the second crystal region 62 can display different waveform characteristics on the photoelectric conversion device 10, so that a layer of crystals in the detector in which the γ particles are obtained can be accurately determined, thereby ensuring the accuracy of the DOI of the γ particles when converting energy in the crystals and ensuring imaging quality.

Correspondingly, each of the scintillation crystals 70 may include a crystal selected from a group including: a LSO crystal (lutetium silicate crystal), a LYSO crystal (yttrium lutetium silicate crystal), a LFS crystal (lutetium fine silicate crystal), a LaBr3 crystal (bromine Lanthanum crystal), a GSO crystal (gadolinium silicate crystal), a GAGG crystal (gadolinium aluminum gallium garnet crystal), a Ce:YAP crystal (cerium-doped yttrium aluminate crystal) and other crystal materials. Such crystal materials in the group are all fast crystals that are commonly used to meet the technical requirements of TOF.

In an optional implementation, the crystal array 60 may be a matrix array, for example, an N×M array, where N and M are both positive integers greater than 1, such an arrangement ensures a smooth and aesthetic external appearance of the detector. When a plurality of medical detectors 200 are assembled into a detection ring, there is no gap in either the ring direction or the axial direction, so that the detection efficiency of the detector and the sensitivity of the system can be improved.

In an optional implementation, a bottom surface of the crystal array 60 is bonded to the photoelectric conversion device 10, and both side surfaces and a top surface of the crystal array 60 are covered with a reflective layer 40. The reflective layer 40 can completely cover the crystal array layer 60, so as to effectively prevent the external light from entering the detector and affecting the luminous effect of the γ particles in the crystals and ensure the accuracy of the detector. In this embodiment, the reflective layer may include a reflective material with lower light transmittance, such as barium sulfate ($BaSO_4$), ESR film (3M™ Enhanced Specular Reflector), titanium dioxide ($TiO_2$), Teflon, etc. The light transmittances of these materials are generally not higher than 10%, which can almost achieve an effect of opacity.

It should be noted that the bottom surface of the crystal array layer 60 can be understood as being formed by all the bottom surfaces of the scintillation crystals 70. The top surface of the crystal array layer 60 can be understood as being formed by all the top surfaces of the scintillation crystals 70. The side surfaces of the crystal array layer 60 can be understood as being formed by the outer side surfaces of the scintillation crystals 70 located at the outermost side of the crystal array layer 60. Taking an example that the crystal array 60 is arranged as a cube array, the four outer side surfaces and the top surface of the crystal array 60 may be all covered with a reflective layer 40.

In an optional implementation, adhesive material can be provided between the plurality of scintillation crystals 70 of the crystal array layer 60 and the photoelectric conversion device 10. Optionally, the adhesive material may be an adhesive material with a low refractive index (for example, ≤1.6) and a high light transmittance (for example, ≥80%), such as glue liquid, glue film. Using such adhesive material may not affect the projection shape formed on the photoelectric conversion device 10 by the DOI of the γ particles when converting energy in the crystals.

In an optional implementation, the medical detector 200 may further include a light guide component, e.g., an optical waveguide. The light guide component may be disposed between the crystal array layer 60 and the photoelectric conversion device 10 by using the adhesive material, that is, the plurality of scintillation crystals 70 of the crystal array layer 60 and the photoelectric conversion device 10 can both be bonded to the light guide component by the adhesive material. The light guide component can improve the uniformity of crystal light emission. Optionally, the light guide component may be made of glass, and its thickness may be set according to actual needs.

In the medical detector 200, the scintillation crystals 70 can be fast crystals, which can maintain the TOF function. When the plurality of medical detectors 200 are assembled into a detection ring of the PET system, no gap can be generated between two adjacent medical detectors 200 and the detection efficiency may not be reduced. No additional expansion or development is required for photoelectric conversion device, back-end processing circuits, computing processing ability, and electronics, and there is little impact on cost and engineering development.

An embodiment of the present application also provides a medical imaging device, including a detection ring assembled by assembling a plurality of medical detectors 200. The structure of this medical imaging device is similar to the medical imaging device in FIG. 4, which will not be described in detail. It should be noted that the description of the medical detector 200 in the above-mentioned embodiments and examples is also applicable to this medical imaging device.

Exemplary embodiments have been described in detail herein, and examples of which are shown in the accompanying drawings. When the above description refers to the accompanying drawings, unless otherwise indicated, the same numeral in different drawings represents the same or similar element. The embodiments described in the above exemplary embodiments do not represent all embodiments consistent with the present disclosure. On the contrary, they are merely examples of devices consistent with some aspects of the present disclosure as detailed in the appended claims.

The terms used in the present disclosure are only for the purpose of describing particular embodiments and are not intended to limit the present disclosure. The singular forms "a", "said" and "the" used in the present disclosure and the appended claims are also intended to include the majority forms unless the context clearly indicates other meanings. It should also be understood that the term "and/or" as used herein refers to and includes any or all possible combinations of one or more associated items listed.

Although the terms "first", "second", "third", etc. may be used to describe various information in the present disclosure, the information should not be limited to these terms. These terms are only used to distinguish the same type of information from each other. For example, without departing from the scope of the present disclosure, the first information may also be referred to as second information, and similarly, the second information may also be referred to as the first information. Depending on the context, the word "if" as used herein can be interpreted as "when" or "upon" or "in response to determining that".

The foregoing embodiments are only the preferred embodiments of the present disclosure, and do not limit the present disclosure in any form. Although the present disclosure has been disclosed as the above with the preferred embodiments, it is not intended to limit the present disclosure. Anyone who is familiar with this technology, within the scope of not departing from the technical solution of the present disclosure, can use the technical contents disclosed above to make some changes or modifications to equivalent embodiments of equivalent changes. However, within the technical contents of the present disclosure, any simple alterations, equal changes and modifications made to the above embodiments based on the technical nature of the present disclosure should fall within the protection scope of the present disclosure.

What is claimed is:

1. A medical detector comprising:
  a photoelectric conversion device;
  a first crystal array layer comprising a plurality of first scintillation crystals arranged in a first crystal array, the first crystal array layer being disposed over the photoelectric conversion device along a length direction of the first scintillation crystals, a first coupling medium being filled between every adjacent two of the first scintillation crystals; and
  a second crystal array layer disposed over the first crystal array layer along the length direction, the second crystal array layer comprising a plurality of second scintillation crystals arranged in a second crystal array, a second coupling medium being filled between every adjacent two of the second scintillation crystals,
  wherein the first crystal array layer comprises a bottom surface and a top surface along the length direction, and the bottom surface of the first crystal array layer is bonded to the photoelectric conversion device, and the top surface of the first crystal array layer is bonded to a bottom surface of the second crystal array layer,
  wherein a first light transmittance of the first coupling medium is different from a second light transmittance of the second coupling medium,
  wherein a crystal material of the first scintillation crystal is different from a crystal material of the second scintillation crystal, and
  wherein, along the length direction, a length of the first coupling medium corresponds to a length of each of the plurality of first scintillation crystals over the photoelectric conversion device, and a length of the second coupling medium corresponds to a length of each of the plurality of second scintillation crystals over the plurality of first scintillation crystals.

2. The medical detector of claim 1, wherein:
  a higher one of the first and second light transmittances is no lower than 70%, and
  a lower one of the first and second light transmittances is no higher than 10%.

3. The medical detector of claim 1, further comprising:
  adhesive material disposed between the plurality of first scintillation crystals of the first crystal array layer and the plurality of second scintillation crystals of the second crystal array layer.

4. The medical detector of claim 1, further comprising:
  adhesive material disposed between the plurality of first scintillation crystals of the first crystal array layer and the photoelectric conversion device.

5. The medical detector of claim 1, further comprising:
  a light guide adhesively arranged between the first crystal array layer and the photoelectric conversion device.

6. The medical detector of claim 1, wherein the first crystal array layer comprises:
  side surfaces, together with side surfaces of the second crystal array and a top surface of the second crystal array layer, covered with a reflective layer.

7. The medical detector of claim 6, wherein a light transmittance of the reflective layer is no greater than 10%.

8. The medical detector of claim 1, wherein each of the first scintillation crystals comprises a same first crystal selected from a group of crystals comprising: a lutetium silicate crystal, an yttrium lutetium silicate crystal, a lutetium fine silicate crystal, a gadolinium silicate crystal, a lanthanum bromide crystal, a gadolinium aluminum gallium garnet crystal, and a cerium-doped yttrium aluminate crystal, and
  wherein each of the second scintillation crystals comprises a same second crystal selected from the group of crystals.

9. The medical detector of claim 1, wherein an array arrangement of the second crystal array is same as that of the first crystal array, and
  wherein a center distance of adjacent two of the second scintillation crystals is same as that of adjacent two of the first scintillation crystals.

10. A medical imaging device comprising:
  a detection ring assembled by assembling a plurality of medical detectors;
  a centralized data managing board;
  a reconstruction processor;
  a display; and
  a scanning bed,
  wherein each of the plurality of medical detectors comprises:
    a photoelectric conversion device;
    a first crystal array layer comprising a plurality of first scintillation crystals arranged in a first crystal array, the first crystal array layer being disposed over the photoelectric conversion device along a length direction of the first scintillation crystals, a first coupling medium being filled between every adjacent two of the first scintillation crystals; and a second crystal array layer disposed over the first crystal array layer along the length direction, the second crystal array layer comprising a plurality of second scintillation crystals arranged in a second crystal array, a second coupling medium being filled between every adjacent two of the second scintillation crystals, wherein the first crystal array layer comprises a bottom surface and a top surface along the length direction, and the bottom surface of the first crystal array layer is bonded to the photoelectric conversion device, and the top surface of the first crystal array layer is bonded to a bottom surface of the second crystal array layer, wherein a first light transmittance of the first coupling medium is different from a second light transmittance of the second coupling medium, wherein a crystal material of the first scintillation crystal is different from a crystal material of the second scintillation crystal, and wherein, along the length direction, a length of the first coupling medium corresponds to a length of each of the plurality of first scintillation crystals over the photoelectric conversion device, and a length of the second coupling medium corresponds to a length of each of the plurality of second scintillation crystals over the plurality of first scintillation crystals.

11. A medical detector comprising:
a photoelectric conversion device; and
a crystal array comprising a plurality of scintillation crystals arranged in an array, the crystal array being disposed over the photoelectric conversion device along a length direction of the scintillation crystals, the crystal array being divided into a first crystal region and a second crystal region along the length direction of the scintillation crystals, the first crystal region comprising first parts of the scintillation crystals and the second crystal region comprising second parts of the scintillation crystals, a first coupling medium being filled between the first parts of every adjacent two of the scintillation crystals in the first crystal region, and a second coupling medium being filled between the second parts of every adjacent two of the scintillation crystals in the second crystal region, wherein the crystal array comprises a bottom surface and a top surface along the length direction, and the bottom surface of the crystal array is bonded to the photoelectric conversion device along the length direction, wherein a first light transmittance of the second coupling medium is different from that of the first coupling medium, and wherein, along the length direction, a length of the first coupling medium corresponds to a length of the first crystal region over the photoelectric conversion device, and a length of the second coupling medium corresponds to a length of the second crystal region over the first crystal region.

12. The medical detector of claim 11, wherein:
a higher one of the first and second light transmittances is no lower than 70%, and
a lower one of the first and second light transmittances is no higher than 10%.

13. The medical detector of claim 11, further comprising:
adhesive material disposed between the plurality of scintillation crystals of the crystal array and the photoelectric conversion device.

14. The medical detector of claim 11, further comprising:
a light guide adhesively arranged between the crystal array and the photoelectric conversion device.

15. The medical detector of claim 11,
wherein side surfaces of the crystal array and the top surface of the crystal array are covered with a reflective layer.

16. The medical detector of claim 11, wherein each of the plurality of scintillation crystals is selected from a group comprising: a lutetium silicate crystal, an yttrium lutetium silicate crystal, a lutetium fine silicate crystal, a gadolinium silicate crystal, a lanthanum bromide crystal, a gadolinium aluminum gallium garnet crystal, and a cerium-doped yttrium aluminate crystal.

* * * * *